(12) United States Patent
Stefansen

(10) Patent No.: US 10,117,996 B2
(45) Date of Patent: Nov. 6, 2018

(54) STATE CHANGING APPLIANCE FOR A DRUG DELIVERY DEVICE

(71) Applicant: Novo Nordisk A/S, Bagsvaerd (DK)

(72) Inventor: Mads Schenstroem Stefansen, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 560 days.

(21) Appl. No.: 14/653,408

(22) PCT Filed: Dec. 20, 2013

(86) PCT No.: PCT/EP2013/077766
§ 371 (c)(1),
(2) Date: Jun. 18, 2015

(87) PCT Pub. No.: WO2014/096396
PCT Pub. Date: Jun. 26, 2014

(65) Prior Publication Data
US 2015/0343151 A1      Dec. 3, 2015

Related U.S. Application Data

(60) Provisional application No. 61/740,546, filed on Dec. 21, 2012.

(30) Foreign Application Priority Data

Dec. 21, 2012   (EP) ..................................... 12198913

(51) Int. Cl.
*A61M 5/315*         (2006.01)

(52) U.S. Cl.
CPC .... *A61M 5/31525* (2013.01); *A61M 5/31536* (2013.01); *A61M 5/31575* (2013.01);
(Continued)

(58) Field of Classification Search
CPC .......... A61M 5/31533; A61M 5/31528; A61M 5/3155; A61M 5/31558; A61M 5/31525;
(Continued)

(56) References Cited

U.S. PATENT DOCUMENTS 4,973,318 A * 11/1990 Holm ...................... A61M 5/24
                                                         604/208
5,320,609 A    6/1994 Haber et al.
(Continued)

FOREIGN PATENT DOCUMENTS

CN         1374876 A    10/2002
JP      H11216181 A     8/1999
(Continued)

*Primary Examiner* — Nathan R Price
*Assistant Examiner* — Justin L Zamory
(74) *Attorney, Agent, or Firm* — Wesley Nicolas

(57) ABSTRACT

A system comprising a state changing appliance and a drug delivery device, the state changing appliance comprising first interface means for rotationally locking to a first exterior portion of the drug delivery device, second interface means for rotationally locking to a second exterior portion of the drug delivery device, the first exterior portion and the second exterior portion being angularly displaceable relative to one another from a first relative position to a second relative position, which second relative position defines a set dose to be expelled by the drug delivery device, and limiter means for limiting a relative angular displacement between the first interface means and the second interface means.

17 Claims, 11 Drawing Sheets

(52) U.S. Cl.
CPC ............ *A61M 2005/3154* (2013.01); *F04C 2270/0421* (2013.01)

(58) Field of Classification Search
CPC .......... A61M 5/31536; A61M 5/31575; A61M 2005/3154
See application file for complete search history.

(56) References Cited

U.S. PATENT DOCUMENTS

| | | |
|---|---|---|
| 5,569,214 A | 10/1996 | Chanoch |
| 5,674,204 A | 10/1997 | Chanoch |
| 6,001,089 A | 12/1999 | Burroughs et al. |
| 6,277,101 B1 | 8/2001 | Kirchhofer et al. |
| 2004/0030293 A1 | 2/2004 | Gurtner |
| 2011/0034878 A1 | 2/2011 | Radmer et al. |
| 2012/0165742 A1 | 6/2012 | Plumptre |

FOREIGN PATENT DOCUMENTS

| | | |
|---|---|---|
| WO | 9324160 A1 | 12/1993 |
| WO | 99/64092 A1 | 12/1999 |
| WO | 01/54757 A1 | 8/2001 |
| WO | 03086512 A1 | 10/2003 |
| WO | 2011073302 A1 | 6/2011 |

\* cited by examiner

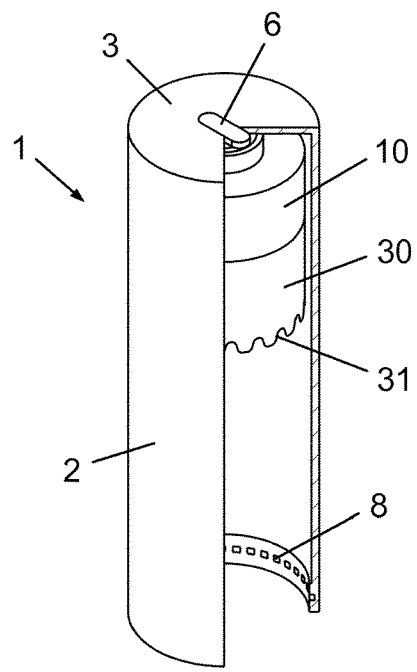
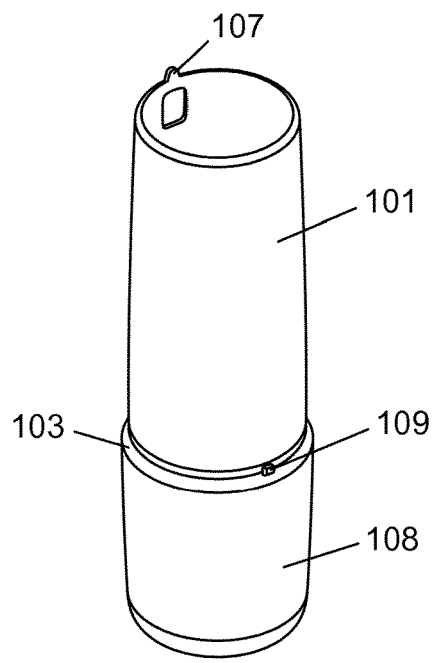
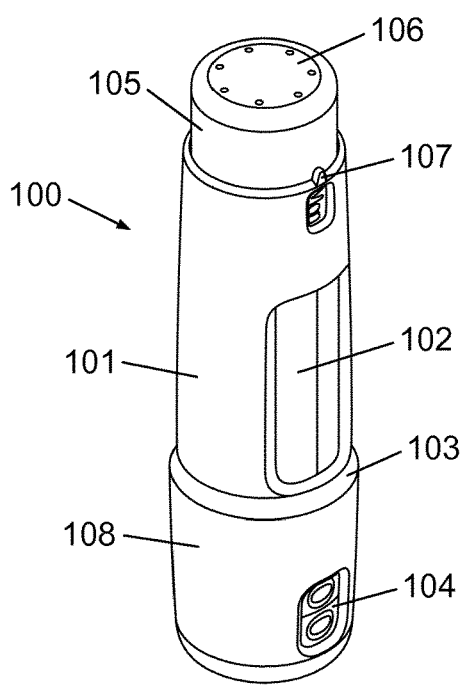
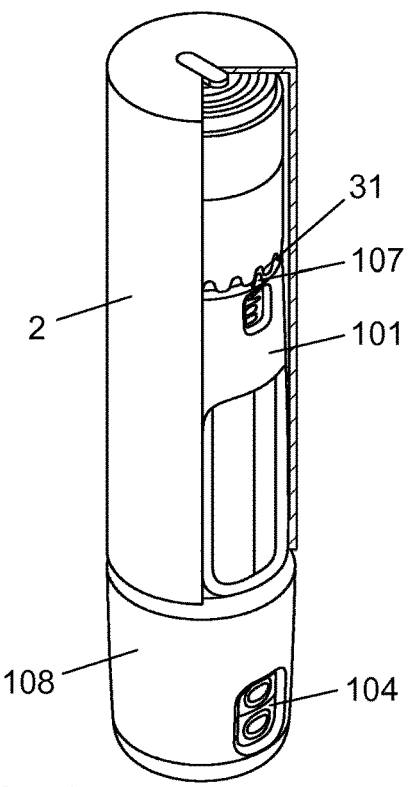
Fig. 1a
Fig. 1b
Fig. 1c

STATE CHANGING APPLIANCE FOR A DRUG DELIVERY DEVICE

CROSS-REFERENCE TO RELATED APPLICATIONS

This application is a 35 U.S.C. § 371 National Stage application of International Application PCT/EP2013/077766 (published as WO 2014/096396), filed Dec. 20, 2013, which claims priority to European Patent Application 12198913.1, filed Dec. 21, 2012; this application claims priority under 35 U.S.C. § 119 to U.S. Provisional Application 61/740,546; filed Dec. 21, 2012.

FIELD OF THE INVENTION

The present invention relates generally to handling aids for drug delivery devices, and more specifically to dose setting aids for such devices.

BACKGROUND OF THE INVENTION

Most modern devices for multiple dose delivery of pharmaceutical substances comprise a dose setting mechanism that allows a user to selectively set a dose to be dispensed from a substance containing reservoir. Some treatment regimens require setting and administration of a dose of drug that varies over time, whereas other treatment regimens require repeated setting and administration of a fixed dose of drug. In some cases the fixed dose may need to be adjusted over time, for example during a dosage titration period.

A common type of drug delivery device is the so-called pen injector which is a pen-shaped injection device used for intermittent subcutaneous administration of an active agent. Typically, by such a pen injector the user can turn a dial about a general longitudinal axis to set a desired dose. If by accident too high a dose is set the dial may be reversed and the dose dialed down until the correct dose is reached.

This dose setting procedure requires particular attention from the user because of the importance of correct dosing. Some drugs are so potent that an overdose can be potentially lethal. However, for a person that is recommended to administer the same dose each time the above described procedure may appear somewhat undue, and it would be desirable if that person could set the particular dose each time without paying too much attention to it. Further, for people with reduced eyesight that find it difficult to read the dose scale on a drug delivery device, each dose setting is subject to a risk of eventual erroneous treatment. It would be equally desirable to provide a greater safety in the dose setting phase for this group of people.

WO 99/64092 (Owen Mumford Limited/Eli Lilly and Company) discloses a dose setting device for self-use medical injectors of the kind having a rotary dose setting knob at the rear end of a barrel that can be indexed around from a zeroed position to bring an indicator opposite a mark on a scale. The dose setting device comprises a cup-like adaptor carrying a lug and a magnifying lens. The adaptor is press fitted over the dose setting knob in a particular angular position indicating the desired dose to be set. The adaptor is rotated until the lug meets a stud on the barrel, whereby the movement is arrested and the dose has been set.

While a magnifying lens may aid the visually impaired to some degree and while the solution apparently avoids any potential excessive dialing because once the adaptor is fitted over the dose setting knob it is simply turned until it meets a physical stop, a user of this dose setting device still has to pay attention each time she/he sets a dose because the adaptor must be positioned relative to the dose setting knob in one specific angular orientation, corresponding to the desired dose, regardless of whether the specific dose is the same for each dose setting. Furthermore, with this device it is not possible to set a dose of a size that requires one, or more than one, full revolution of the dose setting knob due to the lug necessarily abutting the stud before the adaptor has been rotated 360° relative to the barrel.

WO 01/54757 (Novo Nordisk A/S) discloses a dose setting limiter for a different type of injection device in which a dose is set by turning a dial about an axis perpendicular to the general longitudinal axis of the device. The dose setting limiter comprises three parts which when arranged in particular relative angular orientations and mounted on the injection device define a pre-selected maximal allowable dose to be set. The maximal allowable dose is preselectable only when the dose setting limiter is disconnected from the injection device, and one of the three parts accordingly comprises the dose scale to allow the pre-selection.

The dose setting limiter, once in place on the injection device, may aid in securing repetitive settings of a dose that does not exceed the pre-selected maximal allowable dose. However, an adjustment of the pre-selected maximal allowable dose is either impossible, because two of the three parts are permanently fastened to one another, or cumbersome, because all three parts are disjointed and must be handled individually by the user after detachment from the injection device. Also, the injection device is in practice unusable without the dose setting limiter because the user cannot see the size of the dialed dose without the dose scale.

SUMMARY OF THE INVENTION

It is an object of the invention to eliminate or reduce at least one drawback of the prior art, or to provide a useful alternative to prior art solutions.

In particular, it is an object of the invention to provide a solution that alleviates the dose setting procedure for people temporarily or permanently in need of multiple delivery of a particular fixed dose of drug.

It is a further object of the invention to provide a solution as described in the above which is flexible to accommodate situations where the particular fixed dose must be adjusted.

It is a further object of the invention to provide a dose setting appliance for people temporarily or permanently in need of multiple delivery of a particular fixed dose of drug which assists a user in remembering a remaining dose to be injected following an injection of a set dose which was smaller than the fixed dose (e.g. relevant in connection with the emptying of the reservoir contents).

In the disclosure of the present invention, aspects and embodiments will be described which will address one or more of the above objects and/or which will address objects apparent from the following text.

In one aspect of the invention a state changing appliance for a drug delivery device is provided, the state changing appliance comprising:
  a first portion adapted to interface with a first exterior portion of the drug delivery device to prevent relative motion in at least one dimension between the first portion and the first exterior portion, and
  a second portion adapted to interface with a second exterior portion of the drug delivery device to prevent relative motion in the at least one dimension between the second portion and the second exterior portion, the first exterior portion and the second exterior portion being displaceable relative to one another in the at least one dimension from a first relative position defining a first state of the drug delivery device to a second relative position defining a second state of the drug delivery device,
wherein the first portion and the second portion are capable of relative motion in the at least one dimension, the relative motion being limited by two spaced apart stops.

In another aspect of the invention a state changing appliance for a drug delivery device is provided, the state changing appliance comprising:
 a first portion configured for rotational interlocking connection with a first exterior portion of the drug delivery device, and
 a second portion configured for rotational interlocking connection with a second exterior portion of the drug delivery device,
the first exterior portion and the second exterior portion being angularly displaceable relative to one another from a first relative position defining a first state of the drug delivery device to a second relative position defining a second state of the drug delivery device,
wherein the first portion and the second portion are capable of relative angular displacement, the relative angular displacement being limited by two angularly spaced apart stops.

The state changing appliance may be adapted for removable attachment to the drug delivery device. Particularly, it may be adapted to be mounted on the drug delivery device to change the state of the drug delivery device and to be dismounted from the drug delivery device subsequently to allow further operation of the drug delivery device.

A state changing appliance according to the present invention allows a user to swiftly and reliably change the state of the drug delivery device without paying any particular attention to the state changing procedure. The state changing appliance is e.g. simply mounted on the drug delivery device, whereby the first portion interlocks with the first exterior portion to prevent relative motion therebetween in the at least one dimension, and the second portion interlocks with the second exterior portion to prevent relative motion therebetween in the at least one dimension, such that when the state changing appliance and a portion of the drug delivery device are moved relative to one another in the at least one dimension from an initial position defined by one of the two stops to a predetermined target position defined by the other of the two stops the first exterior portion and the second exterior portion are automatically displaced relative to one another from the first relative position defining the first state of the drug delivery device to the second relative position defining the second state of the drug delivery device. Thus, the user knows that the state of the drug delivery device has been properly changed when the induced relative motion between the state changing appliance and the portion of the drug delivery device is abruptly stopped.

The state changing appliance may be adapted to cover an outlet end portion (e.g. an injection needle, a needle hub interface or a jet nozzle) of the drug delivery device when interfacing with the first and second exterior portions. It may even be adapted to function as a protective cap for the drug delivery device, e.g. in addition covering at least a portion of a drug containing reservoir, when the drug delivery device is not being used, the state changing appliance thereby serving a dual purpose.

The state changing appliance may be mechanically programmable, i.e. it may be switchable between a non-programmable state in which the two stops are incapable of relative motion, e.g. relative angular displacement, and a programmable state in which the two stops are capable of relative motion, e.g. relative angular displacement. Thereby, in the programmable state of the state changing appliance the extent of relative motion between the first portion and the second portion can be selectively defined by adjustment of the relative positions, e.g. relative angular positions, of the two stops.

Particularly, the state changing appliance may be switchable between the non-programmable state and the programmable state when mounted on the drug delivery device. The drug delivery device may be a dose setting and delivery type of device comprising a dose setting mechanism and display means for conveying information indicating a set dose of drug to be expelled therefrom, allowing the device to be fully functional also without the herein described dose setting appliance. Specifically, the drug delivery device may comprise dose indicia in the form of characters on a mechanical scale adapted to undergo relative motion with respect to a window, or electronic means for displaying dose indicia, such as e.g. a liquid crystal display.

The first state may define any first condition of the drug delivery device and the second state may define any condition of the drug delivery device different from the first condition. For example, if the drug delivery device comprises three reservoirs holding different drugs, or drugs of different potency, the first state may define a condition of the drug delivery device in which it is ready to deliver a volume of drug from a particular one of the three reservoirs, and the second state may define a condition of the drug delivery device in which it is ready to deliver a volume of drug from another of the three reservoirs. In this case the state changing appliance may thus enable a quick and easy switching between drug administration from each of the three reservoirs, the switching i.a. depending on how the state changing appliance is programmed.

Particularly, the first state of the drug delivery device may be a state wherein no dose, or a first non-zero dose, is set, and the second state of the drug delivery device may be a state wherein a dose to be delivered from a drug reservoir, e.g. a second non-zero dose, is set. In that connection the state changing appliance can be viewed as a dose setting appliance, adapted to aid in the setting of a particular dose to be delivered from the drug delivery device.

Accordingly, in a further aspect of the invention a dose setting appliance for a drug delivery device is provided, the dose setting appliance comprising:
 a first portion adapted to interface with a first exterior portion of the drug delivery device to prevent relative motion in at least one dimension between the first portion and the first exterior portion, and
 a second portion adapted to interface with a second exterior portion of the drug delivery device to prevent relative motion in the at least one dimension between the second portion and the second exterior portion,
the first exterior portion and the second exterior portion being displaceable relative to one another in the at least one dimension from a first relative position to a second relative position, which second relative position defines a set dose to be expelled by the drug delivery device,
wherein the first portion and the second portion are capable of relative motion in the at least one dimension, the relative motion being limited by two spaced apart stops.

In a further aspect of the invention a dose setting appliance for a drug delivery device is provided, the dose setting appliance comprising:

a first portion configured for rotational interlocking connection with a first exterior portion of the drug delivery device, and a second portion configured for rotational interlocking connection with a second exterior portion of the drug delivery device, the first exterior portion and the second exterior portion being angularly displaceable relative to one another from a first relative position to a second relative position, which second relative position defines a set dose to be expelled by the drug delivery device, wherein the first portion and the second portion are capable of relative angular displacement, the relative angular displacement being limited by two angularly spaced apart stops.

The dose setting appliance may be adapted for detachable attachment to the drug delivery device. Particularly, it may be adapted to be mounted on the drug delivery device for the dose setting and to be dismounted from the drug delivery device subsequently to allow the set dose to be expelled.

Since when the dose setting appliance and the drug delivery device are coupled relative motion between the first portion and the first exterior portion, respectively between the second portion and the second exterior portion, in the dimension relevant for the setting of a dose is prevented the non-programmable state of the dose setting appliance constitutes a dose setting state providing for ready setting of a predetermined dose, whereas the programmable state of the dose setting appliance constitutes a dose adjustment state providing for selective adjustment of the predetermined dose.

The drug delivery device may comprise a dose dial operatively coupled with the dose indicia, and a dose may be selectively set by rotation of the dose dial, e.g. about a longitudinal axis of the drug delivery device, relative to a chassis or a housing, a display of the dose indicia changing state in response to the operation of the dose dial to reflect a dose increase upon clockwise rotation of the dose dial and a dose decrease upon counter-clockwise rotation of the dose dial (or vice versa). In that case, the first exterior portion of the drug delivery device may be a portion of the chassis or housing and the second exterior portion of the drug delivery device may be the dose dial. Further, the first exterior portion and the second exterior portion, and thereby also the first portion and the second portion, may be angularly displaceable relative to one another about the longitudinal axis.

The drug delivery device may have a generally cylindrical or conical housing extending along a longitudinal axis, and the dose setting appliance may be structured to receive an end portion thereof, e.g. to provide a co-axial alignment of the dose setting appliance with the drug delivery device. Particularly, the drug delivery device may be a pen injection device, i.e. an injection device having a configuration resembling that of a fountain pen. Alternatively, the drug delivery device may for example be a doser type injection device or an infusion pump, in either case having a generally box shaped housing.

In the present context, the term "exterior portion", as used in connection with the drug delivery device, means a portion which is accessible from outside the drug delivery device. It is noted, however, that the particular exterior portion need not be completely exposed, but may e.g. be covered in by some structure.

In a further aspect of the invention a dose setting appliance for a drug delivery device is provided, the dose setting appliance comprising:

first interface means for rotational fixation to a first exterior portion of the drug delivery device, second interface means for rotational fixation to a second exterior portion of the drug delivery device, the first exterior portion and the second exterior portion being angularly displaceable relative to one another from a first relative position to a second relative position, which second relative position defines a set dose to be expelled by the drug delivery device, and limiter means for limiting a relative angular displacement between the first interface means and the second interface means.

A dose setting appliance employing the principles of the present invention allows a user to reliably set a predetermined dose without paying any particular attention to the dose setting procedure. The dose setting appliance is simply mounted on the drug delivery device, whereby the first interface means engages with the first exterior portion to prevent relative rotational motion therebetween, and the second interface means engages with the second exterior portion to prevent relative rotational motion therebetween, and a dose increasing relative motion between the dose setting appliance and the drug delivery device is induced. The desired dose is reached when the dose setting appliance and the drug delivery device are unable to undergo any further dose increasing relative motion.

The first interface means and the first exterior portion may be structured to enable rotational interlocking at a plurality of relative angular orientations of the dose setting appliance and the drug delivery device. Further, the second interface means and the second exterior portion may be structured to enable rotational interlocking at a plurality of relative angular orientations of the dose setting appliance and the drug delivery device. For example, one of the first interface means and the first exterior portion may comprise a circumferentially extending surface having e.g. equidistantly distributed, or being completely covered by, engagement means such as e.g. rough surface areas, adhesive, Velcro hooks or loops, or magnetised areas adapted to receive and hold a surface portion of the other of the first interface means and the first exterior portion. A similar interface may be provided between the second interface means and the second exterior portion.

The provision of such means for enabling rotational interlocking of the first interface means and the first exterior portion, respectively the second interface means and the second exterior portion, at a plurality of relative angular orientations of the dose setting appliance and the drug delivery device results in an arrangement which offers quick and easy dose setting because the predetermined dose can be dialed regardless, or virtually regardless, of how the dose setting appliance is angularly oriented relative to the drug delivery device when coupled thereto, i.e. requiring no particular attention from the user during the handling of the two.

Specifically, the first interface means may comprise a plurality of circumferentially spaced apart first interface structures adapted to receive a first dedicated geometry on the first exterior portion. Alternatively, the first interface means may comprise a first dedicated geometry adapted for reception by one of a plurality of circumferentially spaced apart first interface structures on the first exterior portion. Correspondingly, the second interface means may comprise a plurality of circumferentially spaced apart second interface structures adapted to receive a second dedicated geometry on the second exterior portion, or, alternatively, the second interface means may comprise a second dedicated geometry adapted for reception by one of a plurality of circumferentially spaced apart second interface structures on the second exterior portion.

The first dedicated geometry may be configured to interface with more than one of the plurality of circumferentially spaced apart first interface structures at a time. Correspondingly, the second dedicated geometry may be configured to interface with more than one of the plurality of circumferentially spaced apart second interface structures at a time.

The first interface means may be arranged on a first portion of the dose setting appliance, and the second interface means may be arranged on a second portion of the dose setting appliance, the first portion and the second portion being angularly displaceable relative to one another.

The limiter means may comprise a motion limiting mechanism comprising a first stop surface, a second stop surface circumferentially spaced apart from the first stop surface, and a position indicator adapted to travel between the first stop surface and the second stop surface. The position indicator may be rotationally locked with respect to the first interface means and at least one of the first stop surface and the second stop surface may be rotationally coupled with the second interface means.

In the present context, the phrase "a position indicator adapted to travel between the first stop surface and the second stop surface" is meant to cover any relative motion that brings the position indicator from the one stop surface to the other, i.e. the position indicator itself may for example be stationary while the first stop surface and the second stop surface moves. Further, in the present context, the term "position indicator" covers any structure capable of undergoing a well-defined relative motion between the two stop surfaces. Specifically, the term does not imply any particular length of such structure. The position indicator may e.g. be or comprise a protrusion on a structure carrying the first interface means or, alternatively, a dose arm rotationally locked with respect to the first interface means and capable of non-rotational translational motion perpendicular to the motion between the first stop surface and the second stop surface.

The first stop surface may be arranged on a first dose defining structure and the second stop surface may be arranged on a second dose defining structure. The first dose defining structure may comprise a first engagement structure and the second dose defining structure may comprise a second engagement structure, the first engagement structure and the second engagement structure being capable of interlocking to prevent relative angular displacement between the first dose defining structure and the second dose defining structure. One or both of the first dose defining structure and the second dose defining structure may extend along a longitudinal axis. The longitudinal axis may also be an axis of rotation about which any relative angular displacement between the first dose defining structure and the second dose defining structure takes place.

The first dose defining structure and the second dose defining structure may be axially displaceable relative to one another between a first relative axial position in which the first engagement structure interfaces with the second engagement structure to prevent relative angular displacement between the first dose defining structure and the second dose defining structure, corresponding to the non-programmable state, and a second relative axial position in which the first engagement structure and the second engagement structure are disengaged, allowing relative angular displacement between the first dose defining structure and the second dose defining structure, corresponding to the programmable state.

Such a construction provides for a clear distinction between the two states, because relative motion between the first dose defining structure and the second dose defining structure in one dimension is only allowed after relative positioning of the dose defining structures in another dimension.

The first dose defining structure and the second dose defining structure may be biased towards the first relative axial position. Thereby, the user must consciously manipulate the dose setting appliance to switch it to the programmable state. This assures that no adjustment of the predetermined dose can be inadvertently executed.

The dose setting appliance may comprise a user operable state defining button activatable, e.g. movable, to switch the first dose defining structure and the second dose defining structure between the first relative axial position and the second relative axial position. Such a button will allow for easy switching between the non-programmable state and the programmable state, enabling swift adjustment of the predetermined dose.

Particularly, the state defining button may interface with the second dose defining structure and it may be adapted to depress the second dose defining structure against the biasing force from a compression spring to switch the first dose defining structure and the second dose defining structure from the first relative axial position to the second relative axial position.

The first stop surface and the second stop surface may be biased towards one another, i.e. a biasing torque, e.g. from a torsion spring, may constantly try to minimise the angular distance between the two. In that case, when the dose setting appliance is switched to the programmable state, e.g. by depression of the state defining button, the predetermined dose is automatically reset. The pre-setting of a new predetermined dose may then be carried out by increasing the angular distance between the first stop surface and the second stop surface against the biasing force, and when the desired dose is reached the state defining button may be released, whereby the dose setting appliance may be automatically switched to the non-programmable state, enabling the first engagement structure and the second engagement structure to keep the first stop surface and the second stop surface in check.

The dose arm may shift from a dormant or inactive state to a functioning or active state in response to a coupling of the dose setting appliance to the drug delivery device. For example, a mechanical interaction between a portion of the drug delivery device and a portion of the dose setting appliance during e.g. mounting of the dose setting appliance onto the drug delivery device may shift the dose arm from the dormant state to the functioning state. Particularly, by coupling the dose setting appliance to the drug delivery device the dose arm may be moved from a lowered position to a raised position.

The dormant state may thus be a condition of the dose arm which corresponds to a non-use state of the dose setting appliance and the functioning state may be a condition of the dose arm which corresponds to an in-use state of the dose setting appliance.

The dose arm may be biased towards the dormant state, e.g. by suitable force exerting means such as a spring. However, in the functioning state, except when abutting the second stop surface, the dose arm may be prevented from returning to the dormant state by an engagement with at least one of the first dose defining structure and the second dose defining structure. Thereby, upon being switched to the functioning state the dose arm will remain in the functioning state until it has reached the second stop surface and the dose setting appliance has been decoupled from the drug delivery device. In response thereto, if the dose arm is biased towards the dormant state it will automatically return to the dormant state.

The fact that the dose arm retains its functioning state until it has reached the second stop surface allows the user to transfer a remaining dose portion directly to another drug delivery device and expel it from that device. For example, if a first drug delivery device comprises an end-of-content mechanism that prevents it from being set to deliver a dose which exceeds the dose, $D_r$, remaining in its reservoir, and the programmed predetermined dose, $D_p$, of the dose setting appliance exceeds $D_r$ the dose arm will arrest at an intermediate position between the first stop surface and the second stop surface during the dose setting procedure, the intermediate position corresponding to the dose $D_r$. If the dose setting appliance is then removed from the first drug delivery device and attached to a second drug delivery device a continued dose setting procedure will result in the dose arm travelling from the intermediate position to the end position at the second stop surface, whereby a dose of size $D_p$–$D_r$ is set on the second drug delivery device. The desired dosing can then be carried out, in two sittings, without the user having to calculate any remaining dose to be administered from, and remember the remaining dose to be set on, the second drug delivery device.

The engagement between the dose arm and the at least one of the first dose defining structure and the second dose defining structure may comprise a circumferentially extending radial surface on one of the first dose defining structure and the second dose defining structure, forming a shelf, and a catch portion on the dose arm adapted to interface with the shelf. The dose arm may be configured to move longitudinally between the lowered position and the raised position, e.g. in a purely translational motion or in a pivoting motion, and to snap onto the shelf when reaching the raised position.

The first dose defining structure and the second dose defining structure may each comprise a circular-cylindrical portion, and these portions may be arranged concentrically about a longitudinal axis of the dose setting appliance. The second stop surface may comprise a wall portion or another protruding structure on the circular-cylindrical portion of the second dose defining structure and the shelf may extend from the back of the wall portion, or the another protruding structure, along the circumference of the circular-cylindrical portion of the second dose defining structure and end at a distance from the second stop surface which corresponds to the transversal dimension of the catch portion of the dose arm. This will allow the dose arm to return to the lowered position once it reaches the second stop surface and the dose setting appliance is decoupled from the drug delivery device.

The dose setting appliance may comprise a shell body defining a hollow interior, and one or more of the first dose defining structure, the second dose defining structure, the first interface means, the second interface means, and the limiter means may be arranged in the hollow interior. One or both of the first dose defining structure and the second dose defining structure may be capable of rotation relative to the shell body. Further, one of the first interface means and the second interface means may be capable of rotation relative to the shell body, while the other of the first interface means and the second interface means may incapable of rotation relative to the shell body. As an example thereof, the first interface means may be arranged on an interior rotatable structure and the second interface means may be arranged on the inner wall of the shell body.

The hollow interior may be adapted to accommodate a portion of the drug delivery device. Specifically, the shell body may be a tubular structure adapted to co-axially receive an end portion of a tubular injection device.

The first stop surface and the dose arm may be biased towards one another, at least during dose setting, e.g. via a torsion spring arranged to act between the first dose defining structure and the shell body. This will ensure that each time the dose arm moves from the raised position to the lowered position at the second stop surface, in response to a decoupling of the drug delivery device and the dose setting appliance, it will be automatically returned to the first stop surface.

The engagement between the dose arm and the at least one of the first dose defining structure and the second dose defining structure may be configured to withstand the force biasing the dose arm and the first stop surface towards one another, such that any position of the dose arm in its functioning state is a stable position. This will particularly provide a guaranteed fixed intermediate position of the dose arm in connection with a partitioned administration as described in the above.

For example, ratchet teeth may be circumferentially distributed along the shelf, and the dose arm may comprise a protrusion structured to engage with the toothed shelf surface and to ride over the teeth when subjected to a sufficiently large driving force or torque. Adjacent teeth may be separated a distance correlating with a dose dial increment of the drug delivery device, such that a relative motion between the dose arm and the shelf leading the protrusion from one trough to an adjacent trough during the dialing up of a dose corresponds to a dose increase of one increment, and, conversely, such that a relative motion between the dose arm and the shelf leading the protrusion from one trough to an adjacent trough during the dialing down of a dose corresponds to a dose decrease of one increment. In case the drug delivery device contains an insulin product the dose dial increment may e.g. correspond to ½ or 1 IU.

The at least one of the first stop surface and the second stop surface may be rotationally coupled with the second interface means via a gear mechanism, such that a relative angular displacement between the first portion and the second portion results in a significantly smaller relative angular displacement between the first stop surface and/or the second stop surface and the dose arm.

One non-exhaustive example of a suitable gear mechanism is a planetary gear. The shell body may comprise a central gear in the hollow interior and the at least one of the first stop surface and the second stop surface may be rotationally coupled with the second interface means via at least one planet gear meshing with the central gear.

Particularly, the shell body may comprise a central longitudinally extending shaft structured to interact with two or three gear wheels arranged on the interior rotatable structure. The gear wheels may interact with the first dose defining structure, and the second dose defining structure may be rotationally coupled with the gear wheels via the first dose defining structure, dependent on whether the dose setting appliance is in the non-programmable state or in the programmable state.

The incorporation of a gear mechanism enables setting a dose of a size which requires a relative angular displacement between the first exterior portion and the second exterior portion in excess of 360°, because depending on the gear ratio such an angular displacement may result in a relative angular displacement between the first dose defining structure and the first interface means, and thereby between the first stop surface and the dose arm, of e.g. no more than 60°. The gear mechanism thereby allows for a programming and repetitive setting of practically any predetermined dose (within the dose range offered by the specific drug delivery device) using the dose setting appliance.

In a particular embodiment of the invention a dose setting appliance for a drug delivery device of the type comprising a housing, a reservoir adapted to hold a drug, a dose dial rotatable relative to a portion of the housing to set a dose of drug to be expelled from the reservoir, dose indicia responsive to a rotation of the dose dial relative to the portion of the housing for indicating the set dose, and an expelling mechanism for expelling the set dose is provided, the dose setting appliance comprising:

- a shell body defining a hollow interior adapted to receive a portion of the drug delivery device,
- a first interfacing portion arranged in the hollow interior and structured to engage with the portion of the housing so as to prevent relative rotation between the first interfacing portion and the portion of the housing, the first interfacing portion being capable of relative rotational motion with respect to the shell body,
- a second interfacing portion rotationally locked with respect to the shell body and structured to engage with the dose dial so as to prevent relative rotation between the shell body and the dose dial,
- a first dose defining structure comprising a first displacement limiting surface, the first dose defining structure being arranged in the hollow interior and being capable of relative rotational motion with respect to both the first interfacing portion and the second interfacing portion,
- a second dose defining structure comprising a second displacement limiting surface circumferentially spaced apart from the first displacement limiting surface, the second dose defining structure being arranged in the hollow interior and being capable of relative rotational motion with respect to both the first interfacing portion and the second interfacing portion,
- a position indicator rotationally locked with respect to the first interfacing portion and capable of relative motion with respect to the first dose defining structure and the second dose defining structure between the first displacement limiting surface and the second displacement limiting surface, and
- a clutch mechanism structured to cause a relative rotational motion between the position indicator and the first dose defining structure in response to a relative rotational motion between the first interfacing portion and the second interfacing portion.

In a further aspect of the invention a drug delivery device is provided comprising a dose setting mechanism and a dose setting appliance as described in connection with any of the other aspects of the invention. Particularly, the drug delivery device may be an injection device having a cylindrical or conical housing. The dose setting mechanism may comprise a dose dial. A dose display may be operatively coupled with the dose dial and configured to display a set dose in response to a current angular position of the dose dial relative to the housing.

In a further aspect of the invention a drug delivery system is provided comprising a drug delivery device and a state changing appliance as described in connection with any of the other aspects of the invention. In particular, a system comprising a drug delivery device of the type capable of displaying a set dose of drug to be expelled therefrom, and a state changing appliance structured for detachable attachment to the drug delivery device may be provided, wherein the drug delivery device comprises

- a first exterior portion, and
- a second exterior portion, the first exterior portion and the second exterior portion being capable of undergoing relative angular displacement from a first relative position to a second relative position, the second relative position defining a set dose to be expelled by the drug delivery device, and wherein the state changing appliance comprises

- first interface means, such as e.g. a first coupling structure, for rotational interlocking connection with the first exterior portion,
- second interface means, such as e.g. a second coupling structure, for rotational interlocking connection with the second exterior portion, the first interface means and the second interface means being capable of undergoing relative angular displacement, and
- limiter means adapted to limit the relative angular displacement between the first interface means and the second interface means.

The limiter means thereby defines a maximum possible relative angular displacement between the first exterior portion and the second exterior portion when the state changing appliance is attached to the drug delivery device.

The limiter means may be a motion limiting mechanism comprising a position indicator rotationally fixed with respect to the first interface means, a first abutment surface defining a first extreme position which the position indicator may assume, and a second abutment surface angularly spaced apart from the first abutment surface and defining a second extreme position which the position indicator may assume. At least one of the first abutment surface and the second abutment surface may be rotationally coupled with the second interface means.

The drug delivery device may comprise a drug reservoir, either replaceable or integrated and non-replaceable, having a drug outlet, and a portion of the shell body may cover the drug outlet when the state changing appliance is attached to the drug delivery device. Thereby, the user is forced to remember to remove the state changing appliance from the drug delivery device before commencing a drug administration, and a system is provided in which the dose setting procedure is clearly separated from the dose delivery procedure to avoid any confusion or erroneous handling.

In a further aspect of the invention a drug delivery system is provided comprising:

- a drug delivery device comprising a dose setting mechanism for setting a dose by inducing relative angular displacement between a first component portion and a second component portion, the dose setting mechanism comprising indicia for displaying a set dose corresponding to a current angular position of the first component portion relative to the second component portion, and
- a dose setting appliance removably attachable to the drug delivery device, the dose setting appliance comprising a first portion configured for being rotationally locked with respect to one of the first component portion and the second component portion, when the dose setting appliance is attached to the drug delivery device, and a second portion configured for being rotationally locked with respect to the other of the first component portion and the second component portion, when the dose setting appliance is attached to the drug delivery device, wherein the first portion and the second portion are capable of undergoing relative angular displacement, and wherein the dose setting appliance further comprises dose setting limitation means defining a maximum relative angular displacement between the first portion and the second portion.

In the foregoing the invention has been described in connection with a desire to provide a solution for easy setting of a predetermined dose. It is noted, however, that the invention is equally applicable for ensuring a particular maximum dose setting, e.g. allowing a healthcare professional or another subject to pre-set the dose setting appliance along the lines set out in the present specification to prevent a user from setting a dose which exceeds a certain level. Any dose up to and including the pre-defined maximum dose is then settable by the user.

It is noted that no particular configuration of the state changing appliance is implied by the present specification. While certain shapes may have advantages over others it is clear to the skilled person that the mere presence of the first coupling means, the second coupling means, and the limiter means entails no principled restriction on the design of the state changing appliance.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 1a is a perspective view of a system according to an exemplary embodiment of the invention, showing a dose setting appliance before attachment to a drug injection device, where a portion of the dose setting appliance has been removed to reveal interior portions and elements thereof, FIG. 1b is a perspective view of the injection device housing and the dose dial, rotated 180° from the view in FIG. 1a, FIG. 1c is a perspective view of the dose setting appliance, as seen in FIG. 1a, after attachment to the injection device.

In the figures like structures are mainly identified by like reference numerals.

DESCRIPTION OF EXEMPLARY EMBODIMENTS

Figure 2:
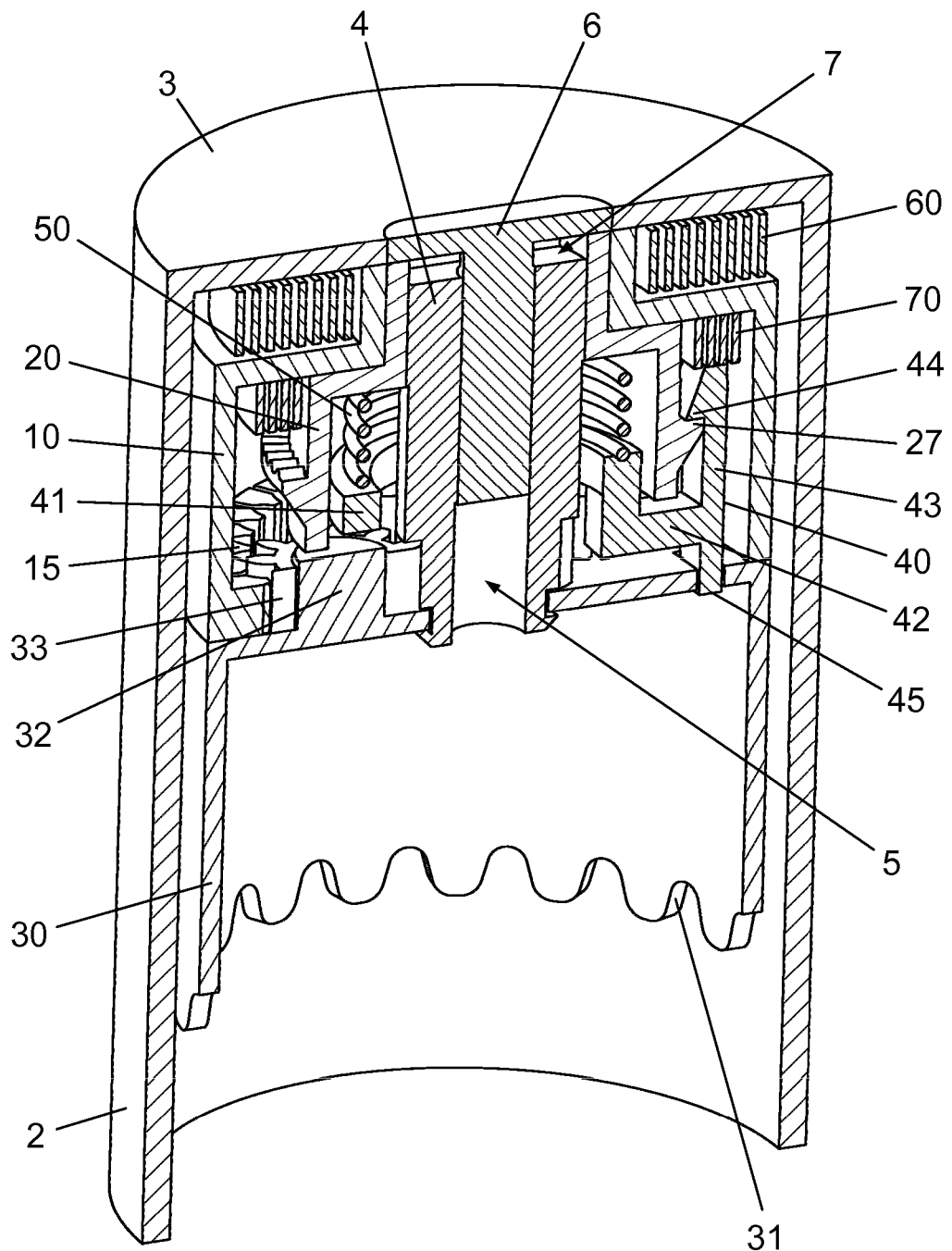
FIG. 2 is a longitudinal section perspective view of the top portion of the dose setting appliance.

When in the following relative expressions, such as "upwards" and "downwards", are used, these refer to the appended figures and not necessarily to an actual situation of use. The shown figures are schematic representations for which reason the configuration of the different structures as well as their relative dimensions are intended to serve illustrative purposes only.

FIG. 1a is a perspective view of a system according to an exemplary embodiment of the invention, showing a dose setting appliance before attachment to an injection device 100. In this embodiment the dose setting appliance takes the form of a cap 1 and it comprises a tubular shell body 2 and a top face 3. A portion of the shell body 2 has been removed to reveal an interiorly positioned cap base 10 and a cap chassis 30. The cap chassis 30 is provided with a corrugated end 31 and the shell body 2 has a plurality of notches 8 circumferentially equidistantly distributed along its inner wall. A push button 6 is arranged centrally in the top face 3.

The injection device 100 comprises a housing 101 accommodating a cartridge 102 which holds a volume of a drug, e.g. a glucose regulating agent such as insulin. The proximal end portion of the housing 101 constitutes a handgrip 108 which accommodates a dose dial mechanism comprising a dose dial ring 103 and a dose display 104 operatively coupled thereto such that the dose indicia presented at the dose display 104 changes in response to a rotation of the dose dial ring 103 about the longitudinal axis of the injection device 100. At the distal end of the housing 101 an axially protruding knob 107 is arranged. The injection device 100 further comprises an injection needle which in the present view is covered by a retractable needle shield 105 and a pierceable rubber septum 106.

The cap 1 is switchable between two general states, a programmable state and a non-programmable state, by selective operation of the push button 6. The shown view, in which the push button 6 is flush with the top face 3, reflects the non-programmable state of the cap 1. By depression of the push button 6 the cap 1 is switched to the programmable state. In the programmable state, when the cap 1 is attached to the injection device 100 and a dose is being dialed on the injection device 100 internal components (not visible in FIG. 1a) of the cap 1 will take up certain relative positions corresponding to the dialed dose. When the desired dose is reached and the cap 1 is switched back to the non-programmable state the internal components in question are locked in those certain relative positions, whereby the cap 1 has been programmed to enable quick and easy re-setting of a predetermined dose (the pre-dialed desired dose) during subsequent use with the injection device 100. The details of the programming of the cap 1 are provided below.

FIG. 1b shows the housing 101 and the dose dial ring 103 from an angle opposite to the one in FIG. 1a. Specifically, it is seen that the dose dial ring 103 carries a protuberance 109.

FIG. 1c shows the cap 1 attached to the injection device 100. The removed portion of the shell body 2 now reveals the rotational interlocking connection between the cap chassis 30 and the housing 101, provided by the engagement between the knob 107 and the corrugated end 31. In this coupled state of the cap 1 and the injection device 100 the protuberance 109 is in engagement with one of the notches 8, providing a rotational interlocking connection between the shell body 2 and the dose dial ring 103 (not visible).

FIG. 2 is a longitudinal section perspective view of the upper or proximal portion of the cap 1, detailing the structure of the predetermined dose setting mechanism. The figure shows the cap 1 in a state in which it is attached to the injection device 100. However, for the sake of clarity the injection device 100 has been omitted from this view.

Formed in unity with the shell body 2 and the top face 3 is a central shaft 4 which extends downwardly from the top face 3, leaving a clearance 7 for limited axial movement of the push button 6. The central shaft 4 is at its distal end coupled to the cap chassis 30 to fix the cap chassis 30 axially in the interior of the shell body 2 while allowing relative rotation between the shell body 2 and the cap chassis 30. The central shaft 4 has a through-going bore 5 adapted to receive and stabilise a tubular portion of the push button 6. The distal end portion of the central shaft 4 is formed as a gear and is adapted for interaction with a set of spur gears 33. In the present embodiment three spur gears 33 are displaced 120° from each other. Each spur gear 33 is adapted to rotate around a stud 32 provided on the proximal end face of the cap chassis 30. The spur gears 33 are in engagement with an internal gear 15 in the cap base 10 and are thus capable of transferring a rotational motion of the shell body 2 to the cap base 10. The gear ratio is chosen to ensure that, in the programmable state of the cap 1, the relative angular displacement between the shell body 2 and the cap chassis 30 required to set the maximum dose deliverable in one go from the injection device 100 causes a relative angular displacement between the cap base 10 and a cap slave 20 of less than 360°.

A dose definer 40 having a ring-shaped base section 41 is arranged about the central shaft 4. A connecting portion 42 extends radially outwards from the base section 41 and carries an axial arm 43. The arm 43 extends axially downwards from the connecting portion 42 through an opening in the proximal end face of the cap chassis 30 and terminates at a distal abutment surface 45 adapted to interface with a portion of the injection device 100 (not shown). The arm also extends axially upwards from the connecting portion 42 and terminates at a proximal hook 44 adapted to engage with a peripheral shelf 27 on the cap slave 20.

A compression spring 50 is arranged about the central shaft 4 between the base section 41 and a stepped portion of the cap slave 20, biasing the dose definer 40 downwards and the cap slave 20 upwards. A motor spring 60 is arranged to apply a torque between the shell body 2 and the cap base 10. The motor spring 20 is tensioned during setting of a dose on the injection device 100. A reset spring 70 is arranged to apply a torque between the cap base 10 and the cap slave 20.

The reset spring 70 is tensioned in the programmable state of the cap 1 during programming of the predetermined dose.

Figure 3A:
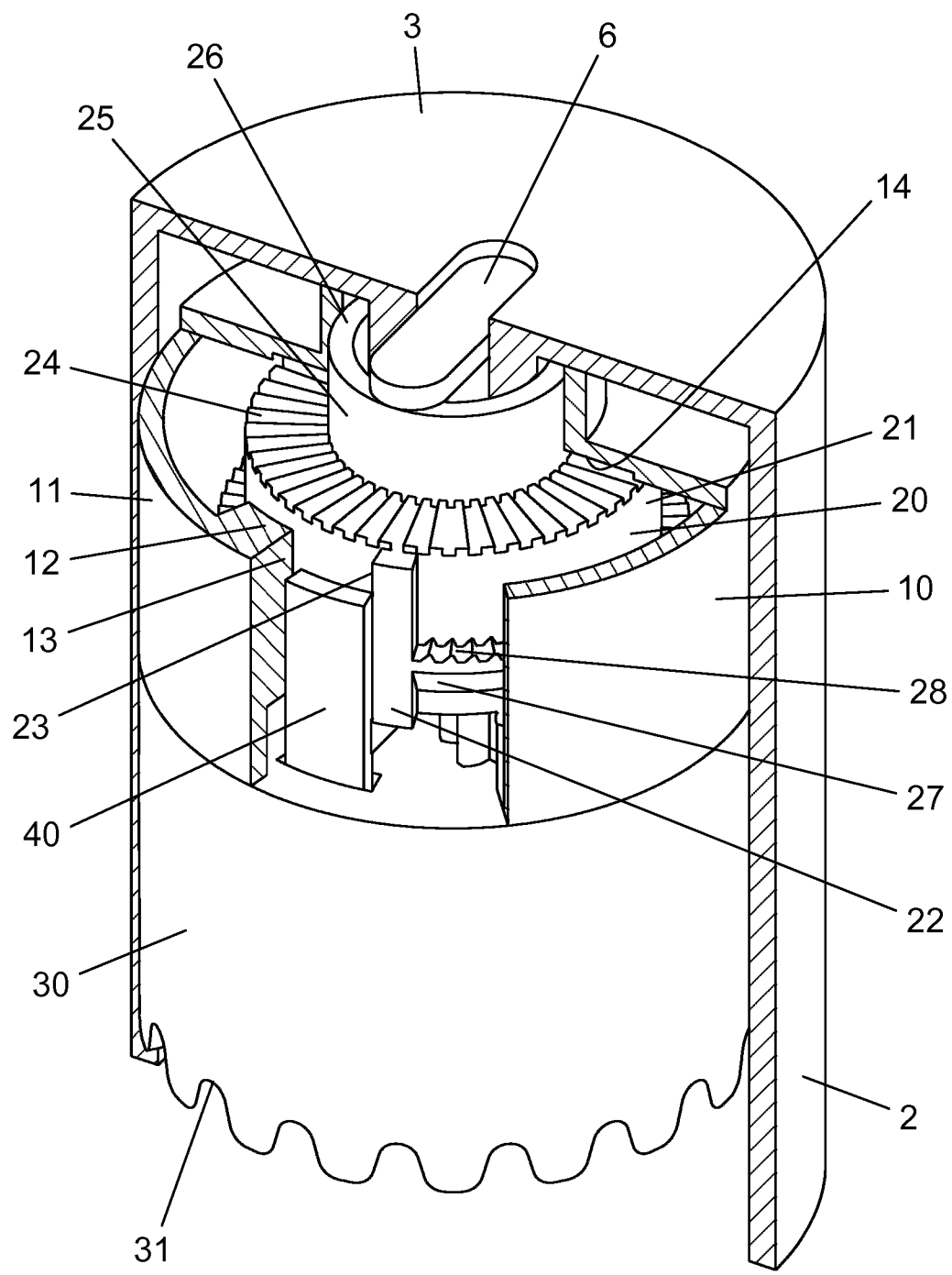
FIG. 3a is a partly perspective, partly longitudinal section view of the dose setting appliance in the programmable state, either initially or after resetting of the predetermined dose.

In FIG. 3a the shell body 2 and a portion of the cap base 10 are seen in a perspective cross-sectional view, while all other components are shown in a normal perspective view. All springs have been removed for the sake of clarity. The figure shows the cap 1 in the programmable state after attachment to the injection device 100 (not shown) but before actual programming of the predetermined dose. The cap base 10 has a cylindrical wall 11, a portion of which has been cut away to reveal an inwardly directed vertical ridge 12, defining a start surface 13 for the travel of the dose definer 40, as well as an outwardly directed vertical ridge 22 on a cylindrical body 21 of the cap slave 20, defining an end surface 23 for the travel of the dose definer 40. In the shown state of the cap 1 the start surface 13 and the end surface 23 are circumferentially spaced apart a distance corresponding to the width of the arm 43, i.e. the arm 43 is sandwiched between the start surface 13 and the end surface 23 before the programming of a predetermined dose.

The stepped portion of the cap slave 20 connects the cylindrical body 21 to a neck 25 having a cylinder end face 26 which in the shown state of the cap 1 is acted upon by the push button 6 to disengage a ribbed collar 24 from a ribbed annular zone 14 on the cap base 10. Thereby, the cap slave 20 and the cap base 10 are capable of relative angular displacement. The shelf 27 is provided with teeth 28 along its entire upper surface for interaction with one or more downwardly directed protrusions (not shown) on the hook 44.

Figure 3B:
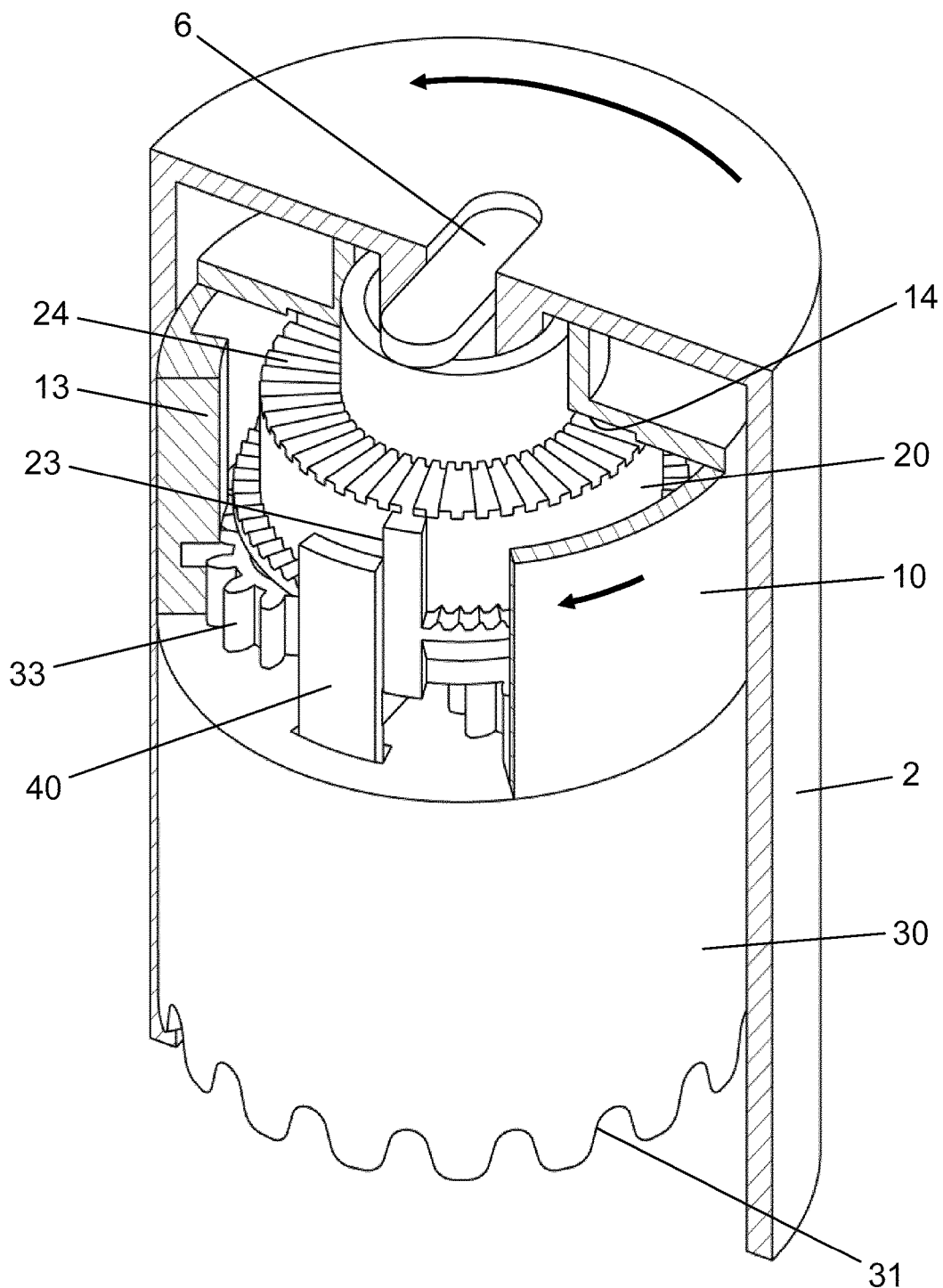
FIG. 3b is a partly perspective view, partly longitudinal section view of the dose setting appliance in the programmable state during setting of the predetermined dose.

FIG. 3b shows the cap 1 during programming of the predetermined dose. While the cap 1 is attached to the injection device 100 (not shown) the shell body 2 is turned counter-clockwise about the longitudinal axis, leading to a, relatively smaller, clockwise rotation of the cap base 10, whereby the start surface 13 is displaced angularly relative to the arm 43 and the end surface 23.

Figure 4:
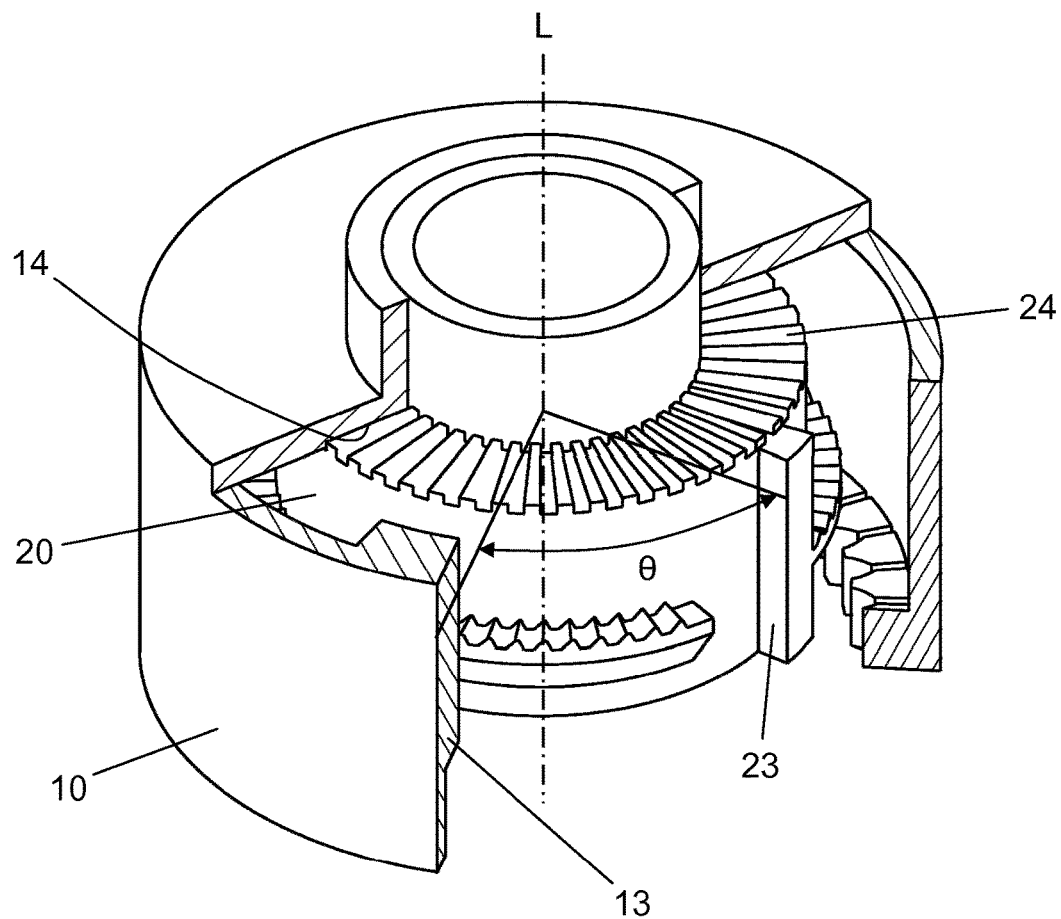
FIG. 4 shows the angular displacement between the stop surfaces in the dose setting appliance.

FIG. 4 shows a resulting angular distance θ between the start surface 13 and the end surface 23 following a programming of a predetermined dose and a switching of the cap 1 to the non-programmable state in which the ribbed collar 24 and the ribbed annular zone 14 are engaged, locking the cap slave 20 rotationally to the cap base 10. The angular distance θ is measured in the plane perpendicular to the longitudinal axis L of the cap 1.

FIGS. 5a-5e show the cap 1 in different situations after programming of a predetermined dose and during use with the injection device 100. The different situations are described below in the section "Use of the dose setting appliance". From FIG. 5a it is seen that the shelf 27 does not extend an entire 360° from the vertical ridge 22 but ends at a distance from the end surface 23 corresponding to the width of the arm 43, whereby a gap 29 is established enabling axial passage of the hook 44 from above the shelf 27 to below the shelf 27 only when the arm 43 abuts the end surface 23.

Figure 6:
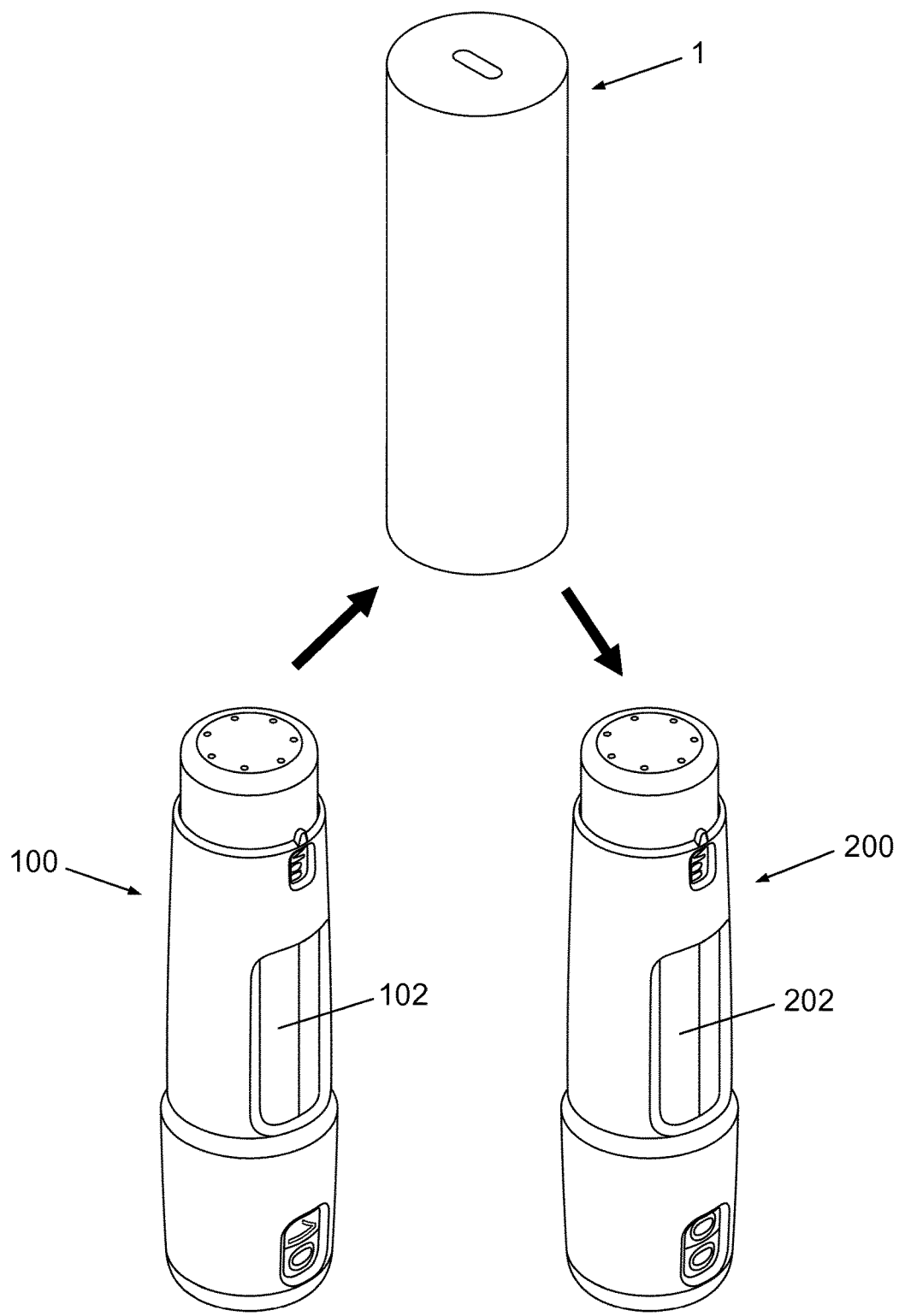

FIG. 6 sketches the use of the cap 1 in a split dose situation, where the predetermined dose programmed thereinto exceeds the last dose remaining in the injection device 100. The figure indicates a specific situation where the cartridge 102 has 10 units of the contained drug left to be administered and where the cap 1 has been programmed to set a dose which is higher than 10 units. The cap 1 has been used on the injection device 100 during the setting of the 10 units and is being moved to a new injection device 200 for a setting of the residual dose portion up to the predetermined or programmed dose. The mechanism enabling this use of the cap 1 is described in detail in the below.

Use of the System

The following describes a use of the cap 1 with the injection device 100. To enable a user to swiftly set the same dose each time a drug administration is needed, the cap 1 must first be programmed for this dose. This is done as described in connection with FIGS. 3a and 3b by placing the cap 1 over the distal end, or needle end, portion of the injection device 100, depressing the push button 6 and turning the shell body 2 relative to the handgrip 108. During the attachment of the cap 1 to the injection device 100 the knob 107 is received in a trough of the corrugated end 31 and the protuberance 109 is received in one of the plurality of circumferentially distributed notches 8, whereby the cap chassis 30 is rotationally locked to the housing 101 and the shell body 2 is rotationally locked to the dose dial ring 103. Further, the dose definer 40 is axially lifted by the needle shield 105 from an inactive position to an active position against the biasing force from the compression spring 50.

The depression of the push button 6 causes an axial displacement of the cap slave 20, against the biasing force from the compression spring 50, a distance equalling the clearance 7, whereby the ribbed collar 24 is brought out of engagement with the ribbed annular zone 14, and the cap slave 20 is thus decoupled from the cap base 10. A counter-clockwise rotation of the shell body 2 relative to the handgrip 108 leads to the central shaft 4 causing a clockwise rotation of the spur gears 33 and thereby of the cap base 10 via the internal gear 15. This relative angular displacement between the shell body 2 and the cap base 10 tensions the motor spring 60 and stores energy therein. Since the cap slave 20 is decoupled from the cap base 10 the result of the counter-clockwise rotation of the shell body 2 relative to the handgrip 108 is an angular clockwise displacement of the start surface 13 relative to both the dose definer 40 and the end surface 23. This relative angular displacement between the cap base 10 and the cap slave 20 tensions the reset spring 70 and stores energy therein. Simultaneously, the dose dial ring 103, driven by the shell body 2, undergoes relative rotation with respect to the cap chassis 30 and the housing 101, causing the dose indicia in the dose display 104 to increase the dose count. When the desired dose is seen in the dose display 104 the push button 6 is released, whereby the compression spring 50 forces the ribbed collar 24 back into engagement with the ribbed annular portion 14 to rotationally lock the cap slave 20 to the cap base 10. At this point the start surface 13 and the end surface 23 are spaced apart a fixed angular distance θ which corresponds to the desired dose to be repeatedly set using the cap 1, and the cap 1 has thus been programmed for this particular dose. When the cap 1 is subsequently removed from the injection device 100 the dose definer 40 is automatically lowered to its inactive position by the compression spring 50, in response to which the motor spring 60 releases its stored energy to automatically rotate the cap base 10 and the cap slave 20 counter-clockwise until the start surface 13 abuts the arm 43. The predetermined, or programmed, dose can now be easily set on the injection device 100 using the cap 1, as will be explained in the following.

Figure 5A:
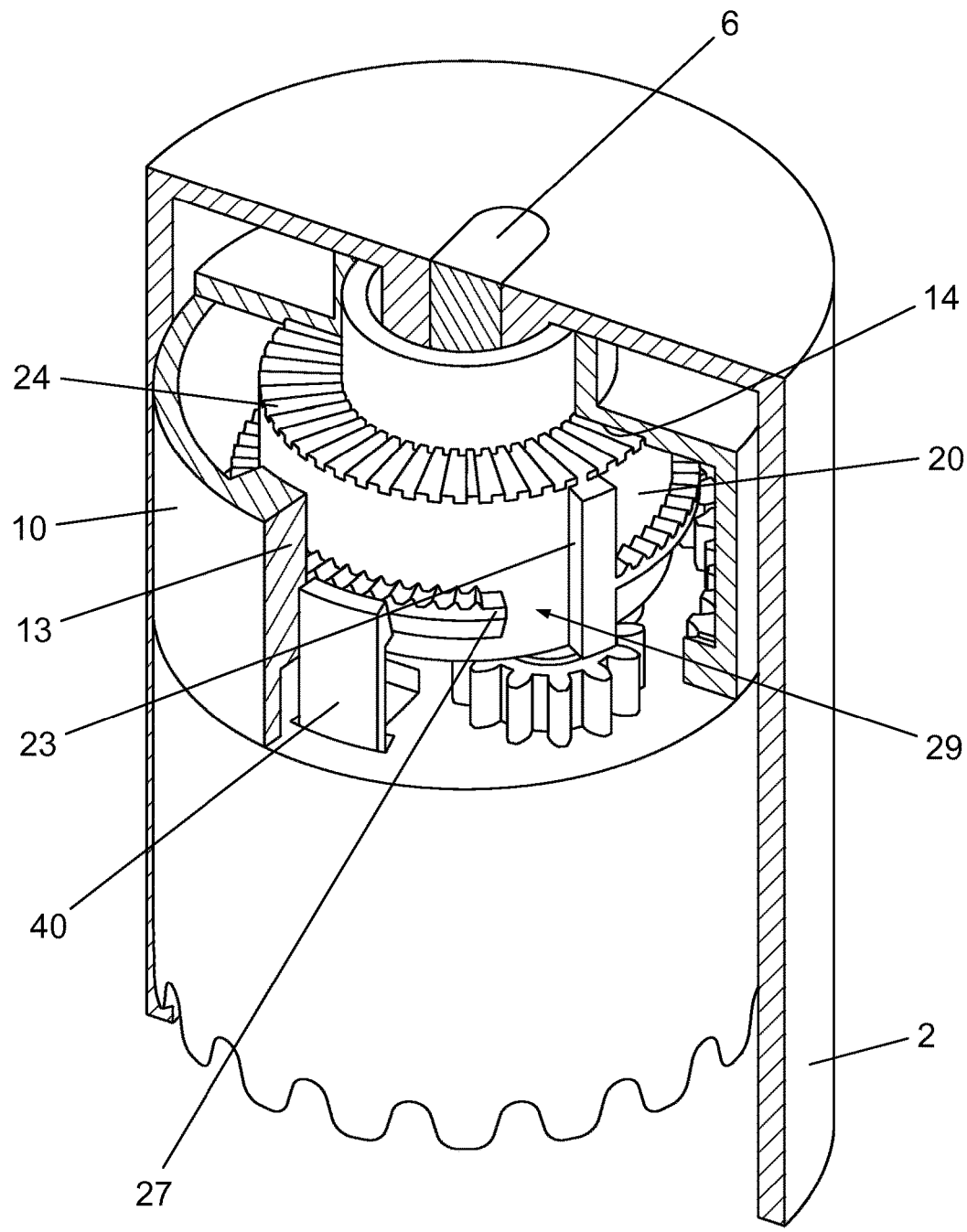
FIG. 5a shows the dose setting appliance in the non-programmable state, before attachment to the injection device.
Figure 5B:
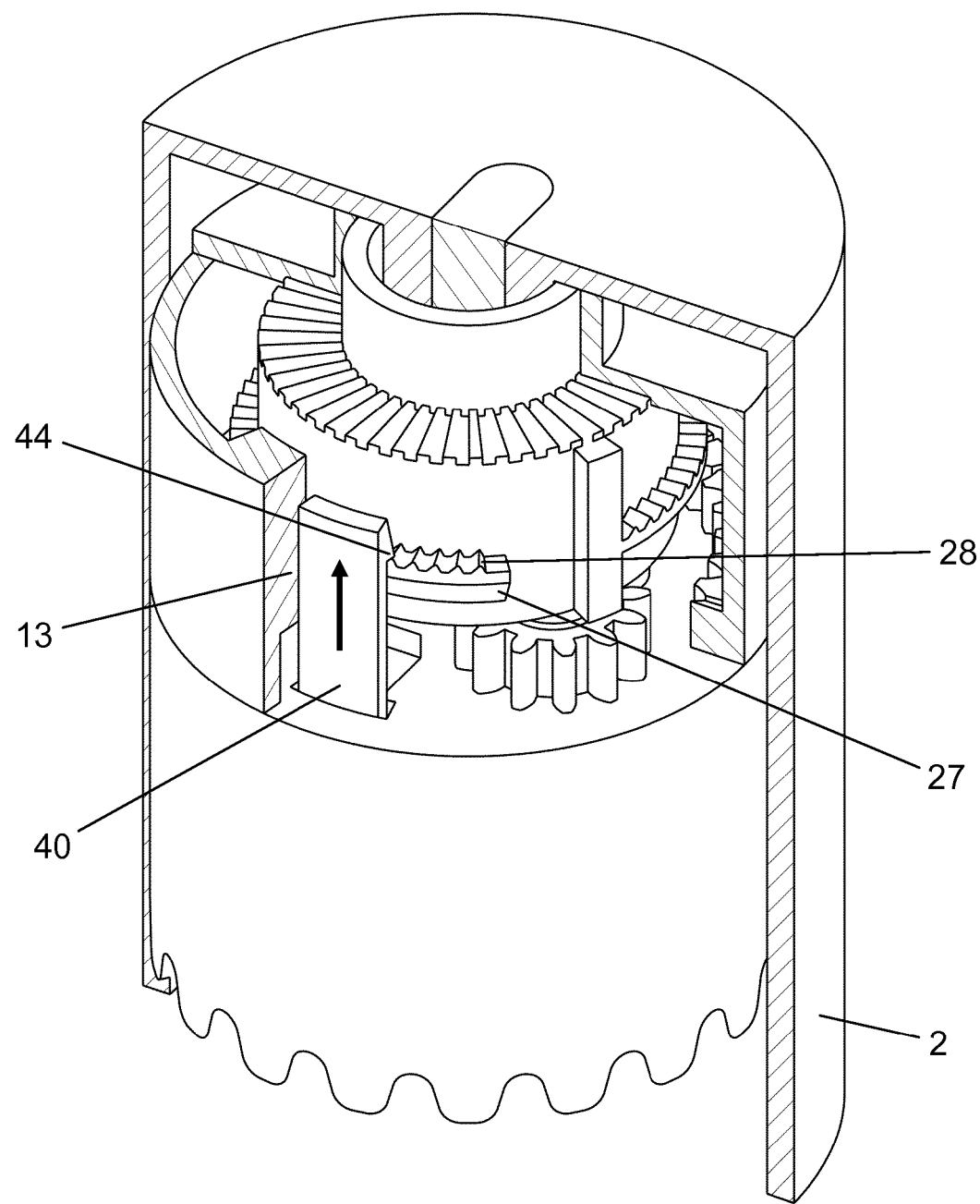
FIG. 5b shows the dose setting appliance after attachment to the injection device.

Upon administration of the set dose from the cartridge 102 the dose display is zeroed and a new dose can be set. If it is desired to set a dose of equal size as the previous one the cap 1 is merely re-attached to the injection device 100, whereby the corrugated end 31 engages with the knob 107, one of the notches 8 engages with the protuberance 109 and the dose definer 40 is lifted axially along the start surface 13 by the needle shield 105 from the inactive position of the hook 44 below the shelf 27 (FIG. 5a) to the active position in which the hook 44 engages with the teeth 28 (FIG. 5b). This tensions the compression spring 50 and stores energy therein. During the movement of the dose definer 40 the somewhat flexible construction provided by the connecting portion 42 causes the arm 43 to deflect radially outwards, and when the dose definer 40 reaches the active position the arm 43 is deflected radially inwards to allow the hook 44 to snap onto the shelf 27.

Figure 5C:
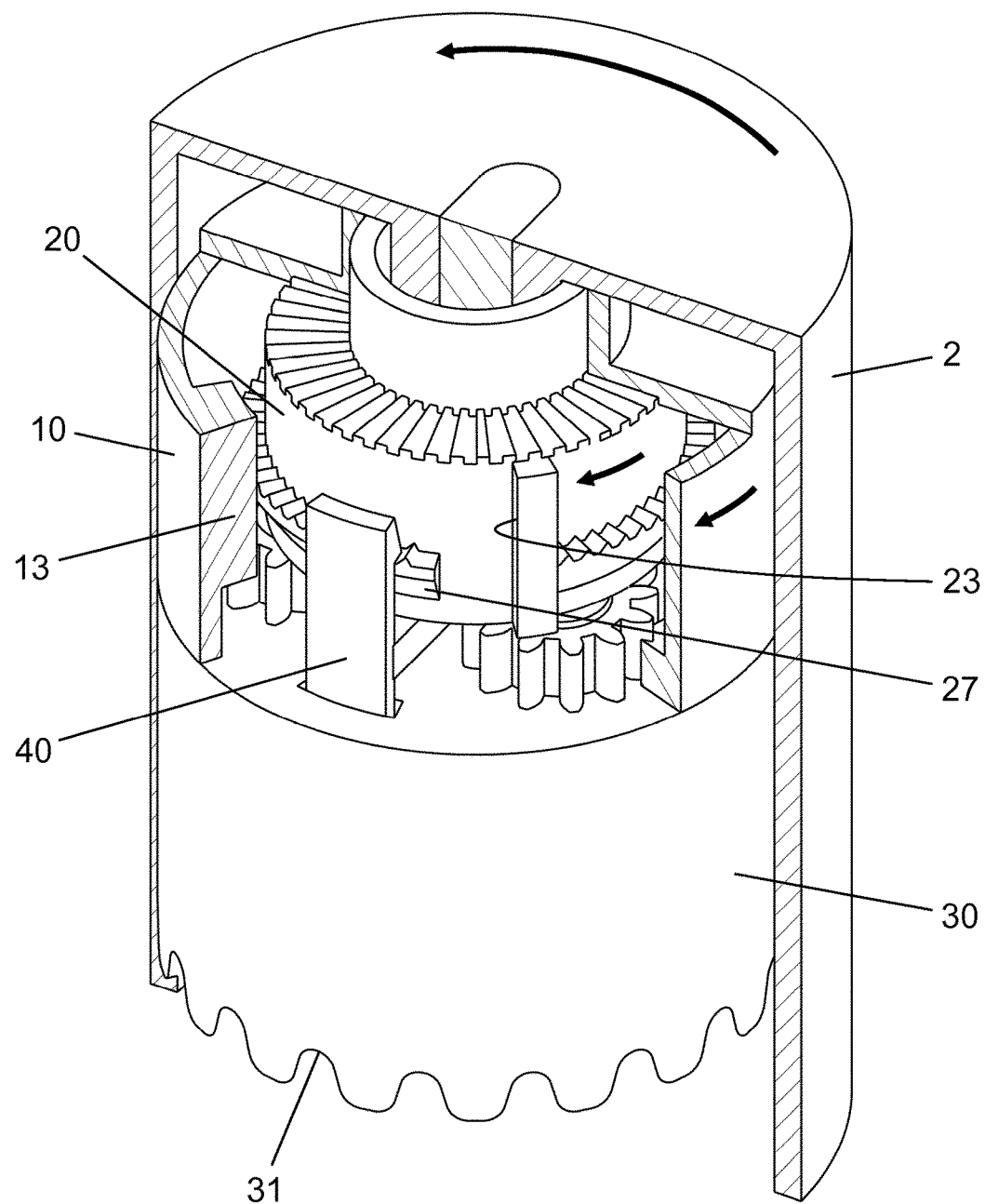
FIG. 5c shows the dose setting appliance during a setting of the predetermined dose on the injection device.
Figure 5D:
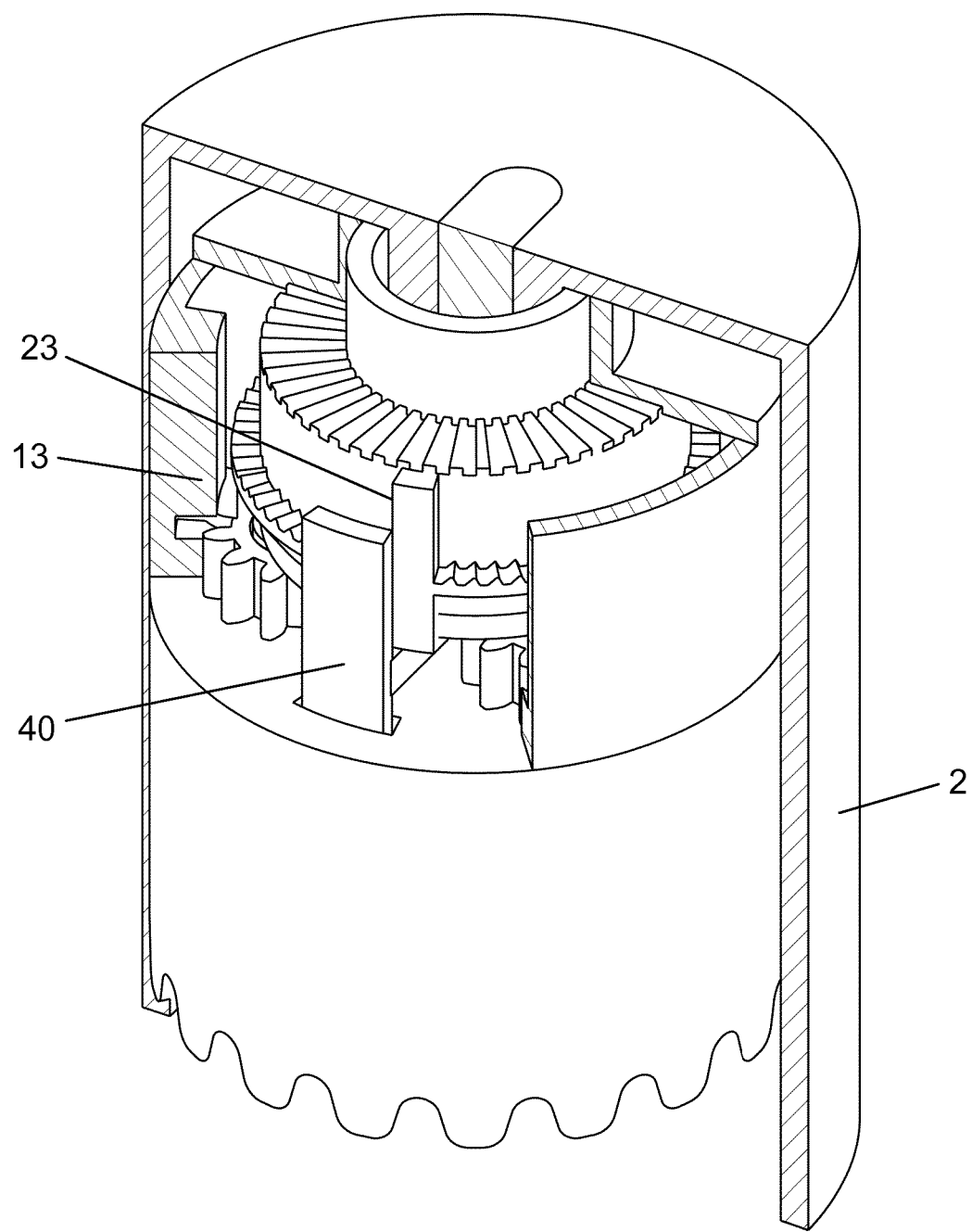
FIG. 5d shows the dose setting appliance when the predetermined dose has been dialed on the injection device.

With the dose definer 40 now activated the user rotates the shell body 2 counter-clockwise relative to the handgrip 108 (FIG. 5c). Due to the gear mechanism and the cap 1 being in the non-programmable state the cap base 10 and the cap slave 20 rotates clockwise, whereby the hook 44 rides over the teeth 28 as the arm 43 travels towards the end surface 23. The relative movement between the shell body 2 and the cap base 10 tensions the motor spring 60 and stores energy therein. Without paying any particular attention to the change of the dose indicia in the dose display 104 the user simply rotates the shell body 2 relative to the handgrip 108 until further rotation is impossible, corresponding to when the arm 43 moves into abutment with the end surface 23 (FIG. 5d). At this point the dose definer has undergone a relative motion with respect to the cap base 10 and the cap slave 20 from the start surface 13 to the end surface 23, which correlates with a relative motion between the dose dial ring 103 and the housing 101 required to set a dose equalling the predetermined dose. In other words, the user simply attaches the cap 1 to the injection device 100 and rotates the shell body 2 relative to the handgrip 108 until a distinct stop is felt, whereby the desired dose is set.

Figure 5E:
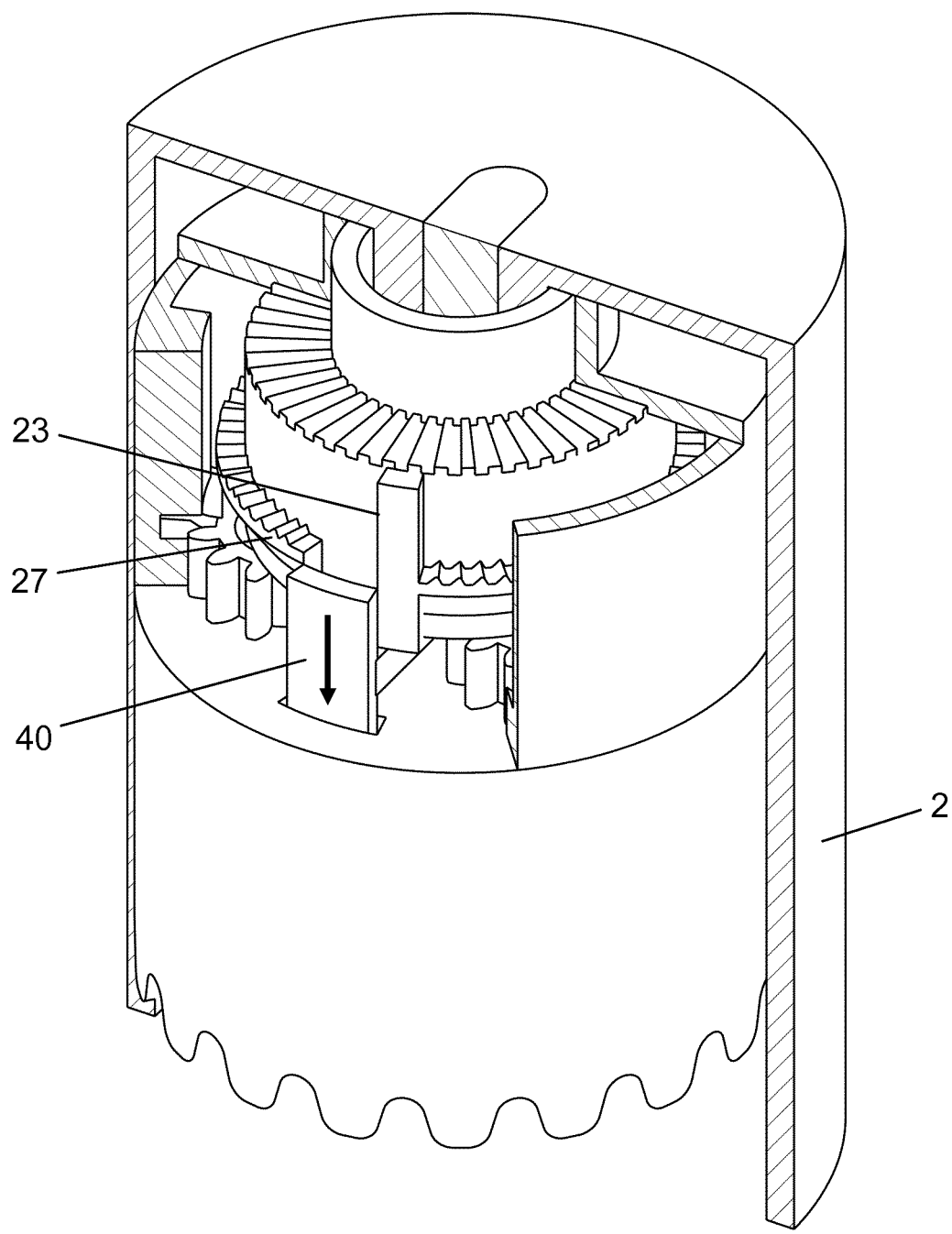
FIG. 5e shows the dose setting appliance immediately following detachment from the injection device, and FIG. 6 sketches the use of the dose setting appliance in a split dose situation, where the predetermined dose exceeds the last dose remaining in the injection device.

The cap 1 is now detached from the injection device 100, whereby the needle shield 105 is removed from the abutment surface 45 and the arm 43 slides downwards through the gap 29 under the influence of the compression spring 50 (FIG. 5e). When the hook 44 reaches the inactive position below the shelf 27 the motor spring 60 releases its stored energy and rotates the cap base 10 and the cap slave 20 counter-clockwise until the arm 43 abuts the start surface 13 (FIG. 5a). The cap 1 is thus automatically readied for a new dose dialing upon detachment from the injection device 100, provided that a dose equalling the predetermined dose has been set.

When the settable dose remaining in the cartridge 102 is smaller than the predetermined dose the end-of-content mechanism in the injection device 100 will prevent the arm 43 from reaching the end surface 23 during the dose setting (because it will prevent further rotation of the dose dial ring 103 relative to the housing 101) and instead cause it to take up an intermediate position along the shelf 27 between the start surface 13 and the end surface 23, e.g. corresponding to FIG. 5c. When the cap 1 is then removed from the injection device 100 the arm 43 will remain in the intermediate position because the shelf 27 prevents the compression spring 50 from moving the dose definer 40 axially downwards and the interaction between the one or more protrusions on the hook 44 and the teeth 28 prevents the motor spring 60 from rotating the cap base 10 and the cap slave 20 relative to the dose definer 40.

The user can now attach the cap 1 to the new injection device 200 and the residual dose to be delivered from a cartridge 202 housed therein is simply set by rotating the shell body 2 about the longitudinal axis of the injection device 200 in a manner similar to the one previously described until a distinct stop is felt when the arm 43 reaches the end surface 23. The predetermined dose can then be administered as a split dose where a first portion is delivered by the injection device 100 and the remaining portion is delivered by the injection device 200. Thereby, no drug is being wasted and the user does not have to calculate and remember the residual dose to be set on the new injection device 200.

The predetermined dose may be changed at any time by depression of the push button 6 to decouple the cap slave 20 from the cap base 10. If the cap 1 is attached to the injection device 100 when the push button 6 is depressed the predetermined dose can be selectively increased or decreased by counter-clockwise, respectively clockwise, rotation of the shell body 2 relative to the handgrip 108. If the cap 1 is detached from the injection device 100 when the push button 6 is depressed the reset spring 70 will release its stored energy and urge the vertical ridge 12 and the vertical ridge 22 towards one another to sandwich the arm 43 between the start surface 13 and the end surface 23. The cap 1 is thereby automatically reset to the non-programmed state shown in FIG. 3a.

The invention claimed is:

1. A system comprising a drug delivery device of the type capable of displaying a set dose of drug to be expelled therefrom, and a state changing appliance structured for detachable attachment to the drug delivery device,
   wherein the drug delivery device comprises:
      a first exterior portion, and
      a second exterior portion, the first exterior portion and the second exterior portion being capable of undergoing relative angular displacement from a first relative position defining a first state of the drug delivery device to a second relative position defining a second state of the drug delivery device, and
   wherein the state changing appliance comprises:
      a first coupling structure configured for rotational fixation with respect to the first exterior portion, wherein the first coupling structure is configured to engage with the first exterior portion in a first rotational interlocking connection, and wherein one of the first coupling structure and the first exterior portion comprises a plurality of circumferentially spaced apart first interface structures and the other of the first coupling structure and the first exterior portion comprises a first dedicated geometry adapted for engagement or abutment with one or more of the plurality of circumferentially spaced apart first interface structures,
      a second coupling structure configured for rotational fixation with respect to the second exterior portion, the first coupling structure and the second coupling structure being capable of undergoing relative angular displacement, and the second coupling structure is configured to engage with the second exterior portion in a second rotational interlocking connection at a plurality of relative angular orientations of the state changing appliance and the drug delivery device, and wherein one of the second coupling structure and the second exterior portion comprises a plurality of circumferentially spaced apart second interface structures and the other of the second coupling structure and the second exterior portion comprises a second dedicated geometry adapted for engagement or abutment with one or more of the plurality of circumferentially spaced apart second interface structures, and
      a limiter mechanism adapted to define a maximum for the relative angular displacement between the first coupling structure and the second coupling structure.

2. A system according to claim 1, wherein the drug delivery device further comprises a housing and a dose dial rotatable relative to the housing to set a dose to be delivered from the drug delivery device, and wherein the first exterior portion is rotationally fixed with respect to the housing and the second exterior portion is rotationally fixed with respect to the dose dial.

3. A system according to claim 1, wherein the state changing appliance further comprises a tubular shell body being open at one end and having a hollow interior, the hollow interior being structured to accommodate a portion of the drug delivery device, when the state changing appliance is attached to the drug delivery device.

4. A system according to claim 3, wherein the drug delivery device comprises a drug reservoir having a drug outlet, and wherein a portion of the shell body covers the drug outlet when the state changing appliance is attached to the drug delivery device.

5. A system according to claim 1, wherein the limiter mechanism comprises a position indicator rotationally locked with respect to the first coupling structure, a first abutment surface defining a first extreme position of the position indicator, and a second abutment surface angularly spaced apart from the first abutment surface and defining a second extreme position of the position indicator, at least one of the first abutment surface and the second abutment surface being rotationally coupled with the second coupling structure.

6. A system according to claim 5, wherein the state changing appliance is switchable between a non-programmable state in which the first abutment surface and the second abutment surface are rotationally locked relative to one another and a programmable state in which the first abutment surface and the second abutment surface are capable of relative rotational motion.

7. A system according to claim 6, wherein the first abutment surface is arranged on a first dose defining structure and the second abutment surface is arranged on a second dose defining structure, the first dose defining structure comprising a first engagement structure and the second dose defining structure comprising a second engagement structure, and wherein the first dose defining structure and the second dose defining structure are arranged concentrically about a longitudinal axis and are capable of relative axial displacement between a first relative axial position in which the first engagement structure interfaces with the second engagement structure to prevent relative angular displacement between the first dose defining structure and the second dose defining structure and a second relative axial position in which the first engagement structure and the second engagement structure are disengaged, thereby allowing relative angular displacement between the first dose defining structure and the second dose defining structure.

8. A system according to claim 7, wherein the state changing appliance further comprises a user operable state defining button activatable to switch the first dose defining structure and the second dose defining structure between the first relative axial position and the second relative axial position.

9. A system according to claim 7, wherein the first abutment surface and the second abutment surface are biased towards one another.

10. A system according to claim 7, wherein the position indicator shifts from a dormant state to a functioning state in response to an attachment of the state changing appliance to the drug delivery device, and wherein in the functioning state, before reaching the second extreme position, the position indicator is prevented from returning to the dormant state by an engagement with at least one of the first dose defining structure and the second dose defining structure.

11. A system according to claim 10, wherein the position indicator is biased towards the dormant state, and wherein when in the second extreme position the position indicator shifts from the functioning state to the dormant state in response to a detachment of the state changing appliance from the drug delivery device.

12. A system according to claim 10, wherein the first abutment surface and the position indicator are biased towards one another by a biasing torque, and wherein the engagement between the position indicator and the at least one of the first dose defining structure and the second dose defining structure is adapted to resist the biasing torque.

13. A system according to claim 12, wherein the engagement between the position indicator and the at least one of the first dose defining structure and the second dose defining structure comprises an interface provided with ratchet teeth circumferentially distributed along a radially extending surface, and wherein adjacent teeth are separated a distance which correlates with a dose dial increment of the drug delivery device.

14. A system according to claim 5, wherein the at least one of the first abutment surface and the second abutment surface is rotationally coupled with the second coupling structure via a gear mechanism reducing the ratio of relative angular displacement between the first abutment surface and the position indicator to relative angular displacement between the first coupling structure and the second coupling structure.

15. A system according to claim 14, further comprising a tubular shell body being open at one end and having a hollow interior, the hollow interior being structured to accommodate a portion of the drug delivery device, when the state changing appliance is attached to the drug delivery device, and wherein the shell body carries the second coupling structure and has a central gear in the hollow interior, wherein the first abutment surface is rotationally coupled with the second coupling structure via at least one spur gear meshing with the central gear and an internal gear of the first dose defining structure.

16. A state changing appliance for use in a system according to claim 1.

17. A drug delivery device for use in a system according to claim 1.

* * * * *